United States Patent [19]

Burnett, Jr. et al.

[11] Patent Number: 4,859,601
[45] Date of Patent: Aug. 22, 1989

[54] STREPTOMYCES BGL PROTEIN GENE PROMOTER

[75] Inventors: William V. Burnett, Jr., Manlius, N.Y.; Thomas G. Eckhardt, Collegeville; Louis R. Fare, Lafayette Hill, both of Pa.

[73] Assignee: SmithKline Beckman Corporation, Philadelphia, Pa.

[21] Appl. No.: 820,345

[22] Filed: Jan. 21, 1986

Related U.S. Application Data

[63] Continuation-in-part of Ser. No. 585,946, Mar. 5, 1984.

[51] Int. Cl.[4] .................. C12N 1/00; C12N 15/00; C12N 1/20; C07H 15/12
[52] U.S. Cl. ....................... 435/253.5; 435/172.3; 435/320; 935/6; 935/41; 536/27

[58] Field of Search ............... 435/172.3, 320, 253, 435/253.5; 536/27; 935/6, 41

[56] References Cited
PUBLICATIONS

Reynolds et al., Nature, vol. 293, pp. 625–629, Oct. 22, 1981.
Wahle et al., Chem. Abst. 100: 169184 g (1984).

*Primary Examiner*—Alvin E. Tanenholtz
*Attorney, Agent, or Firm*—Edward T. Lentz; Janice E. Williams; Alan D. Lourie

[57] ABSTRACT

A DNA fragment from *Streptomyces sp.* which contains the Bgl protein (P49) promoter, the P1 promoter, for expressing heterologous genes.

7 Claims, 2 Drawing Sheets

Restriction endonuclease cleavage map of an 8 kb DNA fragment from *Streptomyces lividans* carrying the gene for excretable β-galactosidase

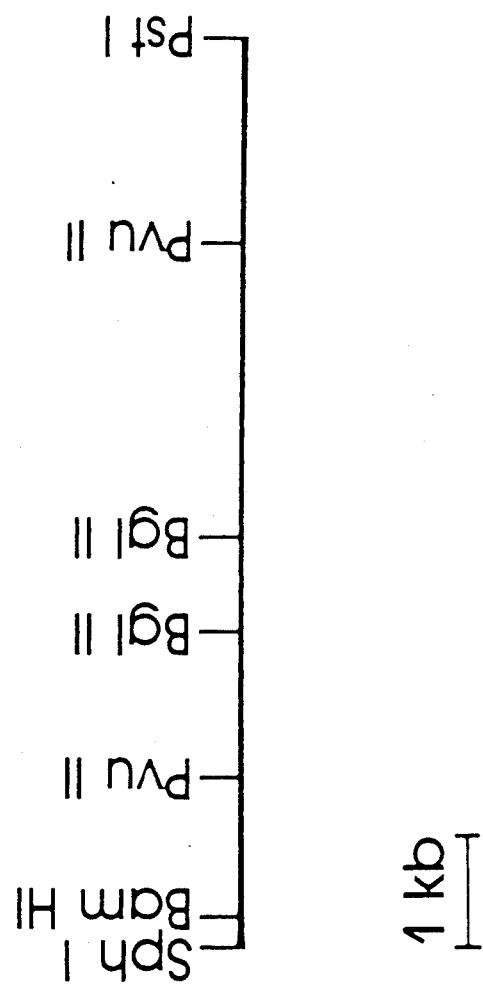
Fig. 1 Restriction endonuclease cleavage map of an 8 kb DNA fragment from Streptomyces lividans carrying the gene for excretable β-galactosidase

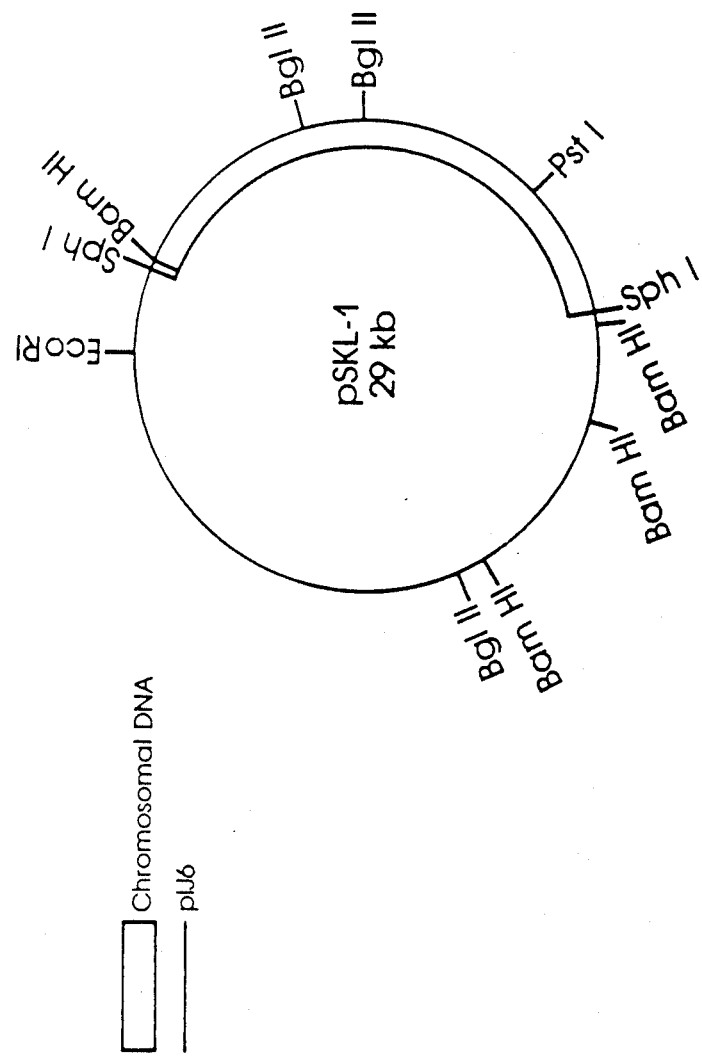
Fig. 2 Restriction endonuclease cleavage map of pSKL-1

STREPTOMYCES BGL PROTEIN GENE PROMOTER

This is a continuation-in-part application of U.S. patent application Ser. No. 585,496, filed Mar. 5, 1984, pending.

FIELD OF THE INVENTION

This invention relates to the field of biotechnology, specifically to genetic engineering. More particularly, the invention relates to cloning of a gene from a Streptomyces species onto suitable vectors and the use of such cloned gene.

BACKGROUND INFORMATION

Although the Actinomycetales produce more than half of the known antibiotics having valuable clinical and other applications as secondary metabolites and, thus, are recognized as a key target for application of gene manipulation techniques, many problems remain to be overcome before specific useful genes are successfully identified and cloned ["Molecular Breeding and Genetics of Applied Microorganisms", Sakaguchi and Okanishi, eds., Academic Press (New York) Kodansha Ltd. (Tokyo) 1980, pgs. 130–131]. Prior work has concerned development of cloning systems or vectors for Streptomycetes [Bibb et al. (1978), Nature 274:398–400; Hayakawa et al. (1979), J. Antibiot. XXXII(12):13-48–1350; Okanishi et al. (1980), J. Antibiot. XXXIII(1):- 88–91; Bibb et al. (1980), Nature 284:526–531; Thompson et al. (1980), Nature 286:525–527; Suarez et al. (1980), Nature 286:527–529; Bibb et al. (1981), Mol. Gen. Genet. 184:230–240]; Bibb (1981), "Microbiology-1981", Schlessinger, ed., American Society for Microbiology, (Washington, D.C.) 1981, pgs. 367–370 and Hopwood et al. (1981), "Microbiology-1981", supra. pgs. 376–379], cloning and expression in Streptomyces sp. of genes derived from Escherichia coli [Schottel et al. (1981), J. Bacteriol. 146:360–368] and cloning of genes from Streptomycetes in Escherichia coli ["Molecular Breeding and Genetics of Applied Microoganisms", supra; pgs. 130–137]. Chater et al. (1982), Current Topics in Microbiol. and Immunol. 96:69–95, review gene cloning in Streptomyces and is incorporated by reference herein as though fully set forth.

SUMMARY OF THE INVENTION

One aspect of the invention is a DNA fragment comprising the Bgl protein gene promoter, such as the fragment which is naturally present within a 0.7 kb Pvu II-Stu I region of S. lividans strain 1326 chromosomal DNA.

Other aspects of the invention include vectors in which the fragments of the invention have been cloned, and microorganisms transformed with such vectors.

All of these embodiments of the invention, as well as others described throughout, are readily attainable uses of this invention and are considered as further aspects of the same invention.

BRIEF DESCRIPTION OF THE DRAWINGS

FIG. 1 is a restriction endonuclease cleavage map of pSKL-1.

DISCLOSURE OF THE INVENTION

The Bgl protein has not been directly observed. Based on sequence data and S1 mapping, the putative protein has a molecular weight of about 49,000. Hence, the putative protein may be referred to as P49. Strains of Streptomyces which are naturally deficient in Bgl protein mRNA transcripts produce transcripts which roughly correspond to a 49,000 MW protein following transformation with the gene expression unit of the invention. The amount of message observed is in the range of amounts of produced during expression of several measurable and isolatable Streptomyces proteins. Thus, it is not clear what the function of the Bgl protein gene expression unit is in nature. Nevertheless, it is useful as a source of a Streptomyces promoter, the Bgl protein gene promoter, which may be referred to as the P1 promoter.

Described below are various DNA fragments of Streptomyces origin which have been discovered to carry the Bgl protein gene expression unit. In particular, the DNA fragments specifically disclosed herein were isolated from S. lividans strain 1326. However, given benefit of this disclosure, one of ordinary skill in the art, using standard DNA probing and other recombinant DNA techniques, can identify and isolate the Bgl protein gene promoter from other strains of Streptomyces including, but by no means limited to, derivatives of strain 1326. Such derivatives are included within the invention. It is also appreciated that derivatives of the disclosed fragments may also carry the Bgl protein gene expression unit. Moreover, it is understood that fragments similar to those disclosed herein, such as fragments differing by the presence or absence of one or more deoxyribonucleotides, including, perhaps, one or more restriction enzyme sites, which differences do not materially affect the biological function of the fragments, for example, gene expression, are included within the invention.

The DNA fragments of the invention are recombinant DNA molecules, that is, DNA sequences, single or double stranded, that have been isolated from the larger molecules in which they are naturally present, such as chromosomal DNA, or from their natural hosts, or which have been partially or wholly synthesized, and which may be fused to other DNA fragments, such as to form expression units or cloning or expression vectors.

The Bgl protein gene expression unit has been found to be located just upstream of the XP55 gene expression unit and of the Streptomyces β-galactosidase gene expression unit, both of which are the subjects of copending patent applications, in S. lividans strain 1326. XP55 is an exported protein having a molecular weight of about 55,000. The Streptomyces gene expression unit confers β-galactosidase activity on hosts deficient in such activity.

The Streptomyces β-galactosidase gene, that is, the gene which causes expression of the Streptomyces β-galactosidase, is naturally present in and was originally isolated from a 16 kb Sph I region of chromosomal DNA of S. lividans strain 1326 which region also carries the Bgl protein and XP55 gene expression units. The 16 kb Sph region has been mapped as follows:

| Restriction Enzyme | Location (kb) |
| --- | --- |
| Sph I | 0 |
| Bam HI | 0.6 |
| Pvu II | 0.9 |
| Bal I | 1.3 |
| Stu I | 1.5 |
| Sal I | 1.8 |

-continued

| Restriction Enzyme | Location (kb) |
| --- | --- |
| Stu I | 1.9 |
| Bcl I | |
| Bgl II | 2.7 |
| Bgl II | 3.7 |
| Pvu II | 5.7 |
| Nru I | 6.5 |
| Pvu II | 7.2 |
| Bcl I | |
| Stu I | 7.7 |
| Pst I | 8.8 |
| Pvu II | 10.3 |
| Pvu II | 10.9 |
| Bam HI | 11.6 |
| Stu I | 12.0 |
| Pvu II | 13.7 |
| Sph I | 15.5 |

This table will be used for further references herein to DNA regions naturally present within the Sph I fragment. So, for example, the 3 kb Pvu II (0.9)-Bgl II (2.7) fragment will be referred to as such whether or not there are additional deoxyribonucleotides upstream and/or downstream thereof.

The entire Bgl protein gene expression unit can be obtained by restricting chromosomal DNA with Pvu II and Bgl II (partial) and selecting for the Pvu II (0.9)-Bgl II (3.7) fragment. It, or other fragments of this region of chromosomal DNA, can be cloned in a vector, such as a phage or plasmid, by known techniques. Alternatively, by way of example, all or part of the gene expression unit can be synthesized. These can be used directly as regulatory or coding sequences or to construct other fragments such as hybrid promoters or hybrid coding sequences or to probe for similar regions in other organisms by standard hybridization techniques.

The promoter region lies between the Pvu II (0.9) and the Stu I (1.9) sites. Based on S1 mapping, it appears that the transcription initiation site begins about 10 bases upstream (5') of the Bal I site. Based on sequence data, there appears to be a translation initiation site about 35 bases downstream (3') of the Bal I site; the termination site is about 135 bases downstream of the Bgl II (3.7) site. The locations of these functions are approximate.

The promoter can be obtained, for example, by restricting chromosomal DNA with Pvu II and Stu I. The Stu I end can be cut back to the translation initiation site, or further, with a restriction endonuclease to produce DNA fragments of the invention in which the promoter region includes sequences through the translation initiation site, through the Shine-Dalgarno sequence, and/or through the transcription start site. The Pvu II-Stu I fragment can also be cut back from the Pvu II end. However, removal of a large number of 5' non-coding sequences reduces promoter efficiency. Other combinations of endonucleases and/or exonucleases will be apparent. For example, the promoter sequence can also be obtained and utilized on a 0.2 kb Taq I-Bal I fragment. Such promoter-containing fragments can be cloned in a plasmid and fused to a heterologous structural gene by known techniques to produce a desired product in Streptomyces hosts as well as in other microorganisms.

For expressing heterologous proteins, it may prove desirable to include a N-terminal coding sequence of Streptomyces origin, such as the coding sequence for a portion of the Bgl protein.

The sequence of an illustrative DNA fragment of the invention derived from *S. lividans* strain 1326, starting from about 50 bases downstream of the Pvu II (0.9) site follows. Preferably, the upstream end of the promoter is at or within a few bases of the Pvu II site. The sequence illustrates a useful promoter region for the Bgl protein.

ACCGCGGCCT GGCCGATCCG GTCCTCGGCC

CCGCCCTGCA CGCCTTCCAC GGCCGGCCCG
    CCCAGCCCTG ACGGTGGCC TCGCTCGCGG
    GCCGGGCGGG CGTCTCCCGG GCGCTGTTCG
    CCAAACGCTT CACCGAGCTG ATGGGCCGCC
    CGCCGCTCGC CTACCTCACC GGATGCCGGA

TGGCCGACGC CGAGGCACTG CTGATCGACA
                                                 |
                                            Taq I

CCGACCTGAG CATCGCCCGG ATCGCCAGGG
CCGTCGGCTA TGCCGACGCC CTCGOCTTCA
GCGCCGCCTT CAAACGCCAC CGGGGCCAGA
GCCCCAGCAC GTTCCGCGCC GCGGCGGCGG
CCTGAACCCC GGCGCGCGGT CCCGCCCACC
CGAGACCGTG CGCCGTCGGA CCCCGGGCAT

ATCCTGATCC CCAGTGGCCA TCGGCTGACG
                                     |
                                 Bal I

AAGGGGTCCG AAGGTGCCGT CG ATG

In an illustrative procedure, DNA from *Streptomyces lividans* strain 1326 [National Collection of Industrial Bacteria, Aberdeen, Scotland, No. 11416; Bibb et al., (1981), *Mol. Gen. Genetics* 184:230-240; Krasilnikov et al., "The Biology of Certain Groups of Actinomycetes", Krasilnikov, ed., Science Press (Moscow) 1965, pgs. 109-110, which contains a gene which codes for the Bgl protein which is naturally excreted in its original strain, is collected by standard techniques, such as the technique described by Chater et al., supra. A DNA fragment containing the gene which codes for an excretable Bgl protein is isolated by treating the DNA with a restriction endonuclease.

The gene isolated as decribed above, and which originated from *Streptomyces lividans* 1326, can be readily expressed in other strains and species of Streptomyces such as *Streptomyces griseus*, *Streptomyces aureofaciens*, *Streptomyces fradiae*, *Streptomyces niveus* and others as well as other microorganisms. *Streptomyces lividans* and *Streptomyces griseus* are the preferred host species.

A variety of vectors are useful in this invention, the choice of an advantageous one being within the ken of one skilled in the relevant art. Examples of usable vectors are plasmid pIJ6 [Thompson et al. (1980), *Nature* 286:525-527], pIJ101 [Chater et al. supra] and others which are capable of replicating in the ultimate host strain and permit facile selection for the presence of the vector in such strain. Likewise, various standard growth media can be employed. The plasmid, pIJ6, is the preferred vector.

Incorporation of a plasmid vector containing the desired DNA fragment into microoganisms can be accomplished by usual transformation methods, although other procedures such as transduction or conjugation may be used with suitable hosts. Such procedures are described in and known to the art.

The following example is intended to provide a detailed description of the present invention and manner of carrying it out, but not to limit its scope, applicability or utility.

EXAMPLE

Chromosomal DNA from *Streptomyces lividans* strain 1326 [Bibb et al. (1981), supra.] was isolated using the procedure described by Chater et al., supra. Plasmid pIJ6 (about 21 kb) isolated from *Streptomyces lividans* [Thompson et al. (1980), supra.] was used as the cloning vector as this plasmid carries the gene for thiostrepton resistance, which is useful as a selective marker to select for the plasmid in a given thiostrepton sensitive strain such as 1326 and its derivatives. Treatment of the chromosomal DNA and the pIJ6 DNA with Sph I restriction endonuclease or Pst I restriction endonuclease yielded DNA fragments having a protruding complementary 3' DNA sequence. The pIJ6 DNA was additionally treated with alkaline phosphatase to prevent regeneration of the cloning vector without an additional DNA insert. The Sph I and the Pst I generated DNA's (5 μg of chromosomal DNA, 1 μg of pIJ6 DNA) were ligated separately at 16° C. for 7 days using standard procedures. The ligated DNA's were transformed substantially according to the procedure described by Chater et al., supra., using about $2 \times 10^7$ protoplasts derived from *Streptomyces lividans* strain 1326-9, a nitrosoguanidine induced mutant of strain 1326 lacking any excreted β-galactosidase activity. The protoplasts were spread onto regeneration medium plates and incubated for 18-24 hours at 28° C. The plates were overlaid with a soft agar mixture (0.4% agar in water) containing 100 μg/ml of thiostrepton to select for transformed offspring and 150 μg/ml of X-gal. The plates were incubated for another 2 to 6 days at 28° C., then scored for the appearance of characteristic blue colonies.

Of over 10,000 thiostrepton resistant colonies resulting from the Sph I cloning, 9 turned blue; from about the same number of colonies resulting from the Pst I cloning, one turned blue. The plasmid DNA of all the blue colonies was isolated and analyzed.

Both plasmid DNA from the Sph I and the Pst I cloning had one common 9 kilobase DNA fragment (Sph I (0)-Pst I (8.8)) derived from the chromosome and not previously present on the pIJ6 plasmid. Initially, it was believed, based on what was believed to be the structure of pIJ6, that said 9 kb region contained the Streptomyces β-galactosidase gene. The total Sph I insert was believed to comprise only about 10 kb. As shown in further examples below, it was subsequently discovered that although the gene is located on the Sph I insert, the Pst I-Sph I fragment is not the 9 kb fragment originally identified, but rather is a 6.5 kb fragment located downstream thereof.

A 32 kilobase plasmid derived from the Sph I cloning was termed "pSKL-1". Cleavage by the restriction endonucleases was carried out in the standard manner. The plasmid derived from the Pst I cloning was termed "pX". pSKL-1 is represented by the restriction endonuclease cleavage map show in FIG. 1.

The isolated plasmid DNA from pSKL-1 was used to transform *Streptomyces lividans* 1326-9. Over 70% of the thiostrepton resistant offspring showed an excreted β-galactosidase activity, indicating the presence and expression of the gene on the plasmid. The enzyme levels of cell extracts of the pSKL-1 transformed strain, strain 1326-9/pSKL-1, were increased, in some cases, 100 times, thus showing the presence of the gene on the plasmid. Results of one experiment are given in Table 1, below.

TABLE 1

| | β-GALACTOSIDASE ACTIVITY (nmoles/mg protein/min) CARBON SOURCE IN GROWTH MEDIUM | | |
|---|---|---|---|
| STRAIN | GLUCOSE | LACTOSE | GALACTOSE |
| 1326 | 12 | 76 | 184 |
| 1326-9 | 7 | 24 | 302 |
| 1326-9/pSKL-1 | 372 | 843 | 1242 |

As indicated in Table 1, a few 1326-9 cultures produced more unexcreted β-galactosidase in the presence of galactose than some 1326 cultures.

Transformants harboring the pSKL-1 plasmid produced darker blue colonies than the original 1326 strains, demonstrating the utility of the DNA fragment containing the β-galactosidase gene in the construction of high expression vectors.

β-galactosidase expression from a plasmid is less stable in strain 1326-9 than in strain 1326. This is believed to be due to recombination with chromosomal DNA. pSKL-1, as discussed above, carries the Bgl protein gene expression unit.

To demonstrate utility of the Bgl protein gene promoter in expressing heterologous coding sequences, a 0.2 kb Taq I-Bal I fragment (see, sequence, above) was inserted by means of Bam HI linkers into a Bgl II site in a lacZ expression vector, downstream of a terminator and upstream of a lacZ coding sequence. Plasmids carrying the Bgl protein gene promoter in both orientations were obtained. A β-galactosidase-negative *S. lividans* strain 1326 mutant was transformed with both plasmids as well as a control plasmid lacking any promoter region.

Transformants harbring the promoter region in correct orientation exhibited intracellular β-galactosidase activity at a level of about 960 nmoles/mg protein/min. Transformants harboring the promoter in incorrect orientation showed intracellular β-galactosidase activity equivalent to about 10 nmoles/mg protein/min. Transformants harboring the control plasmid did not exhibit significant levels of β-galactosidase activity.

*Streptomyces lividans* strains 1326 and 1326-9 and a strain containing pIJ6 are publicly available from various sources. To further ensure availability, these strains have been deposited with the Agricultural Research Culture Collection in Peoria, Ill. on June 1, 1982, and assigned accession Nos. 15091, 15090 and 15092, respectively.

While the above description is illustrative of the invention and of the preferred embodiments thereof, the invention is not limited to the precise embodiments illustrated herein, but rather includes all modifications thereof coming within the scope of the following claims. In particular, the invention is not limited to fragments having restriction endonuclease sites or DNA sequences as illustrated, inasmuch as such sites and sequences can vary or be varied without materially affecting the invention.

What is claimed is:

1. A DNA fragment consisting essentially of the Streptomyces Bgl protein gene promoter.

2. The DNA fragment of claim 1 in which the promoter is derived from a 16 kb Sph I region of Streptomyces lividans chromosomal DNA, the promoter in its natural state being upstream of a gene for an excretable β-galactosidase in the region.

3. The DNA fragment of claim 2 in which the promoter is derived from a 0.7 kb pvu II-Stu I region of *S. lividans* strain 1326 chromosomal DNA.

4. A recombinant DNA vector comprising the promoter of claim 1.

5. The vector of claim 2 having a heterologous coding sequence fused in frame to the promoter.

6. A microorganism transformed with the vector of claim 4.

7. The microorganism of claim 6 which is a Streptomyces.

* * * * *